United States Patent [19]

Vaillancourt

[11] 4,127,131
[45] Nov. 28, 1978

[54] HUB ASSEMBLY FOR USE IN THE FILTRATION OF FLUIDS AND METHOD OF MAKING THE SAME

[75] Inventor: Vincent L. Vaillancourt, Livingston, N.J.

[73] Assignee: Johnson & Johnson, New Brunswick, N.J.

[21] Appl. No.: 807,854

[22] Filed: Jun. 20, 1977

[51] Int. Cl.² ............... A61M 5/00; A61M 5/04; B01D 35/00
[52] U.S. Cl. .................... 128/221; 29/451; 210/448; 210/479; 210/497 R; 210/DIG. 3
[58] Field of Search ............... 210/445, 446, 448, 499, 210/DIG. 23, 463, 479; 128/218 N, 221

[56] References Cited
U.S. PATENT DOCUMENTS

| 807,547 | 12/1905 | Fliegel | 210/445 |
|---|---|---|---|
| 3,817,389 | 6/1974 | Weichselbaum | 210/448 |
| 3,862,036 | 1/1975 | Simmons | 210/499 X |
| 3,970,084 | 7/1976 | Raines et al. | 210/448 X |

Primary Examiner—Frank A. Spear, Jr.
Assistant Examiner—Richard W. Burks
Attorney, Agent, or Firm—Richard J. Rodrick

[57] ABSTRACT

A hub assembly for use in the filtration of fluids comprising a hub with a tapered bore extending therethrough, and a filter membrane in the bore. The filter membrane has a first portion extending across the bore and a second portion extending from the first portion in substantial contact with the hub around the bore. Means within the bore presses the second portion into tight contact with the hub around the bore to secure the filter membrane therein.

A method of fabricating a filter membrane and inserting the same into a hub having a bore extending therethrough, the bore being substantially circular in cross section and tapered to define a large opening at its proximal end and a small opening at its distal end, includes forming a substantially flat, circular filter membrane from a filter medium, the membrane having a diameter larger than the large opening of the bore. The membrane is inserted into the tapered bore so that a first portion thereof is substantially perpendicular to the longitudinal axis of the bore, and as the membrane advances and the circular cross-section of the bore decreases, a second portion of the membrane is formed. This second portion is an annular flange extending from the first portion along the hub around the bore, and facing the large opening. The filter member is advanced a sufficient distance in the bore while pressing radially outwardly by a force against the flange so that the first portion is rendered taut by the wiping action of the flange along the hub. When the combination of the tapered bore and the force pressing against the flange provide a secure fit of the membrane within a predetermined location within the bore, the advance of the filter membrane therein is stopped.

12 Claims, 5 Drawing Figures

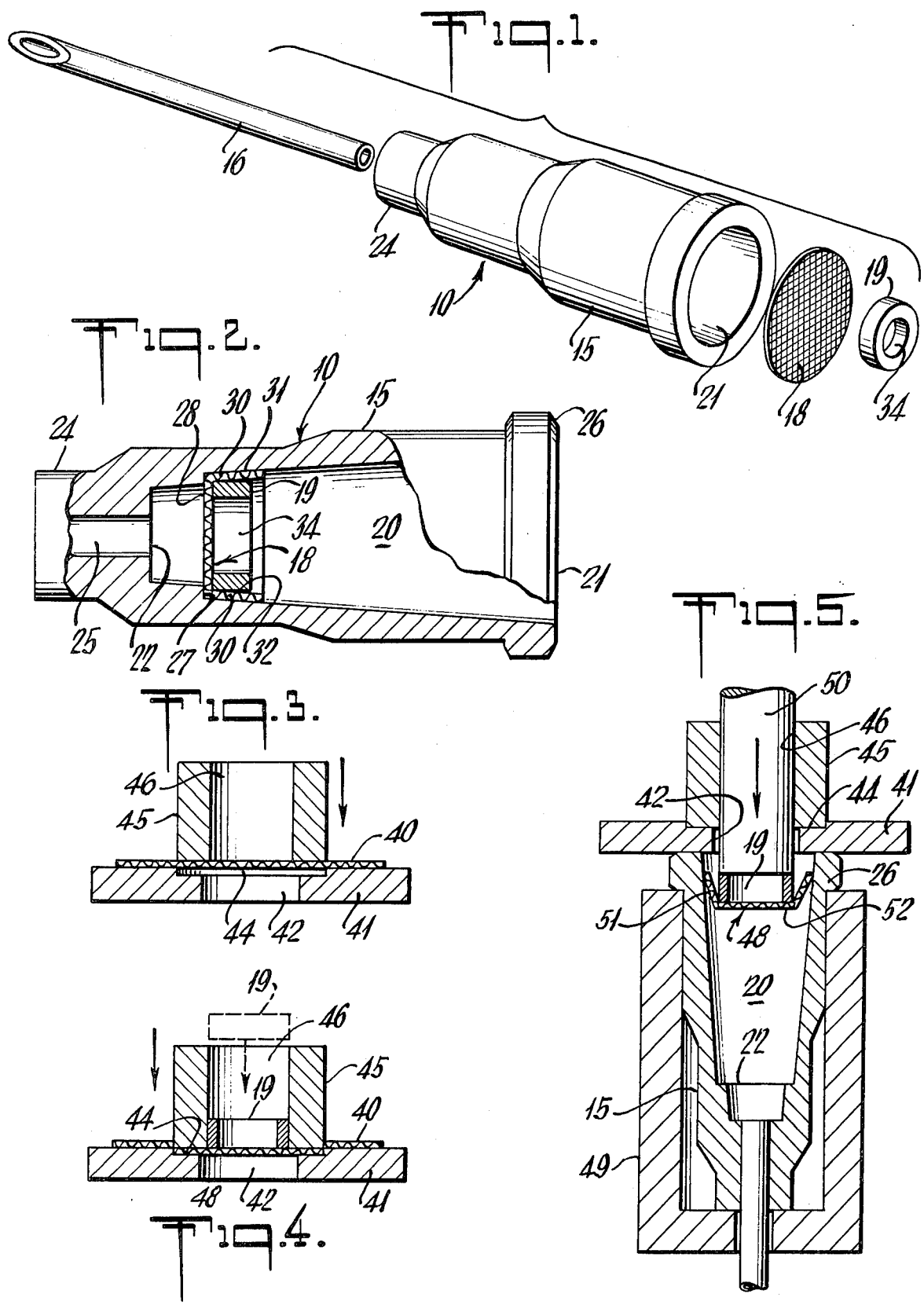

HUB ASSEMBLY FOR USE IN THE FILTRATION OF FLUIDS AND METHOD OF MAKING THE SAME

BACKGROUND OF THE INVENTION

This invention relates to a hub assembly which includes a filter medium therein primarily for use in conjunction with a needle or like instrument for injecting medicaments and the like into a recipient. This invention further pertains to a method of fabricating a filter membrane and inserting the same into a hub.

When liquid medicaments are injected into a patient, it is desirable to deliver the intended liquid with as little impurities or extraneous matter as possible. Oftentimes, even though precautions are undertaken during the administration of liquids to prevent contamination, some impurities, such as particulate matter, are introduced into the liquid medicament for the patient. This occurs, at times, when the liquid medicament is transferred from its supply source to the syringeinjection device. Recognizing that the likelihood of a contaminated medicament is minimal at this stage of administration, it has been found desirable to provide a final precaution immediately prior to injecting the medicament into the patient-recipient. This precaution is accomplished by including a filter medium in the needly assembly itself so that as the liquid passes from the syringe into the needle, a final filtration of the liquid is performed.

Syringe or needle assemblies which include a filter medium for this final filtration precaution are known in a variety of configurations and structures. Particularly, in U.S. Pat. No. 2,864,366, a hypodermic syringe adapter is disclosed which includes a cup-shaped filter element on the tapered end of the adapter. This adapter with the filter is inserted into the tapered bore of a Luer-type hypodermic needle assembly. The mating tapers of the adapter and the needle assembly combine to retain the cup-shaped filter in place. However, it takes the combination of the adapter and the needle assembly to provide this final filtration feature, which is undesirable in a number of aspects. For example, by placing a cup-shaped filter on the tapered end of the adapter, quick insertion into the tapered bore of the needle assembly is required, otherwise nothing retains the filter thereon, with the possibility that it may fall off or require additional handling to maintain it in place, thereby increasing the likelihood of contamination of the filter medium itself. Moreover, having to include the filter element on the adapter device of this patent means that the needle assembly is not a filtered package in itself; in other words, if the filter is left off the adapter when the same is inserted into the needle assembly, this final filtration step will not be achieved. In this regard, it is preferable to provide a needle assembly which includes therein a filter medium as a complete unit.

U.S. Pat. No. 2,857,913 discloses a Luer-type intravenous hypodermic needle assembly in which a disc-like sheet of filter material is retained within a recess formed in the inlet end of the needle hub. A sleeve, press fit in the recess is intended to maintain the filter in operative position. While this needle filter is a complete unit including a filter element, the disc-like nature of the filter is not completely satisfactory in sealing off the recess around its periphery. In this regard, fluid may travel around the peripheral edges of the filter element instead of passing through the same for filtration purposes.

Accordingly, it can be seen that the deficiencies in the various types of needle assemblies with filtration means therein as described above are indicative of the need for improvements in this field.

SUMMARY OF THE INVENTION

The hub assembly of the present invention comprises a hub having a tapered bore extending therethrough. A filter membrane is positioned in the bore and has a first portion extending thereacross. A second portion of the filter membrane extends from the first portion and is in substantial contact with the hub around the bore. Means within the bore presses the second portion into tight contact with the hub around the bore to secure the filter membrane therein.

In the preferred embodiment of the present invention, the bore tapers in generally frusto-conical fashion thereby defining a large opening at the proximal end thereof and a small opening at the distal end thereof. The small opening is adapted to receive a hollow needle or like instrument for conducting fluid from the bore therethrough. The filter membrane is a fine mesh nylon sheet which is flexible, but strong; on each surface of the fine mesh is a thin plastic coating which helps seal the filter to the hub around the bore. The second portion of the filter is an upturned annular flange facing proximally towards the large opening, being in substantially circular contact with the hub around the bore. A retaining ring with an opening therethrough is in annular contact with the inside surface of the flange. As the ring is substantially circular in cross section, smaller than the large opening of the bore, but larger than the small opening, it fits in the tapered bore intermediate the ends thereof until it reaches the position whereat its diameter and the bore diameter are substantially equal. At this position the ring presses the flange tightly against the hub around the bore to secure the filter membrane in a taut condition therein.

Another aspect of the present invention is a method of fabricating a filter membrane and inserting the same into a hub. The hub has a bore extending therethrough which is substantially circular in corss-section and tapered to define a large opening at the proximal end thereof and a small opening at the distal end thereof. The method includes forming a substantially flat, circular filter membrane from a filter medium with a diameter larger than the large opening of the bore. The filter membrane is inserted into the tapered bore so that a first portion thereof is substantially perpendicular to the longitudinal axis of the bore, and as the membrane advances and the circular cross-section of the bore decreases, a second portion of the membrane is formed. This second portion is an annular flange extending from the first portion along the hub around the bore and facing the large opening. By advancing the filter membrane a sufficient distance in the tapered bore and applying a force radially outwardly against the flange, the first portion is rendered taut by the wiping action of the flange along the hub around the bore. When the combination of the tapered bore and the force pressing against the flange provide a secure fit of the membrane at a predetermined location in the bore, the advance of the membrane is stopped.

In one embodiment of the method of the present invention, the filter membrane is formed by punching out a section from a blank of filter medium, and this membrane is inserted into the bore of the hub by advancing a retaining ring against the filter membrane. As the retaining ring has a circular cross-section smaller than the large opening of the bore, but larger than the small opening of the bore, it advances to a position intermediate the ends thereof whereat the diameter of the ring and the diameter of the bore are substantially equal. At this position, the ring produces a radially outwardly pressing force against the flange thereby providing a secure fit of the filter membrane in the bore of the hub.

The hub assembly of the present invention is notably different from hub assemblies for filtration purposes heretofore known in that it includes a unique filter element therein as a completed unit, and provides a secure fit of that filter to interface with the hub to thereby produce a positive seal therein.

In accordance with this invention, the deficiencies of the known hub assemblies, as discussed above, are overcome, and further advantages are offered as well. For instance, as a complete unit, this new hub assembly has the ability to aspirate or inject the fluid medicament. Additionally, the positive mechanical locking of the filter membrane in the hub eliminates the possibility of unfiltered fluid passing into the needle. Aslo, the fabrication of the hub assembly is simple and straightforward, provides an efficient and inexpensive operation and resulting product and may employ conventional production equipment.

Besides use in conjunction with intravenous injection instruments, the hub assembly of the present invention has a variety of other applications, both medical and nonmedical, including, but not limited to, intramuscular injection needs; intravenous additive applications, for adding extra filtered ingredients to a solution container; piggyback filtration, for filtering extra ingredients into the IV line immediately before the injection site; hydrophobic filtration purposes, such as diffusing filtered gases through the membrane; and pipette filter applications.

BRIEF DESCRIPTION OF THE DRAWINGS

FIG. 1 is a perspective view illustrating the elements of a hub assembly of the preferred embodiment of the present invention;

FIG. 2 is a side elevational view of the hub assembly with portions broken away for viewing the internal construction thereof; and FIGS. 3-5 are cross-sectional views schematically illustrating the sequential fabrication of a filter membrane and its insertion into the hub in accordance with the present invention.

DETAILED DESCRIPTION

While this invention is satisfied by embodiments in many different forms there is shown in the drawings and will herein be described in detail a preferred embodiment of the invention, with the understanding that the present disclosure is to be considered as exemplary of the principles of the invention and it is not intended to limit the invention to the embodiment illustrated. The scope of the invention will be pointed out in the appended claims.

Adverting to the drawings, particularly FIGS. 1 and 2, there is shown a hub assembly 10. Hub assembly 10 is comprised of a generally cylindrically shaped tubular hub 15 which is employed to receive the mozzle of a hypodermic syringe for injecting fluids into a patient-recipient. At one end of hub 15, a hollow needle 16 or like cannula is affixed, this needle being the instrument used for piercing the patient's skin in order to administer the medicament. Inserted and secured within hub 15 is a filter membrane 18 through which all fluids pass before entering the patient. A retaining ring 19 is used to insert filter membrane 18 into hub 15, and to provide means for securely maintaining filter element 18 within the hub.

In FIG. 2, the hub assembly 10 is illustrated with its components assembled therein. Hub 15 is formed with a bore 20 extending completely therethrough. Bore 20 is substantially circular in cross-section and tapers in generally frusto-conical fashion to define a large opening 21 at the proximal end thereof, and a small opening 22 at the distal end of tapering bore 20. Preferably, tapering bore 20 is relatively smooth-surfaced to allow easy sliding of the internal components of hub assembly 10. To facilitate the affixation of needle 16 to hub 15, a section 24 of hub 15 extends from the distal end thereof. A substantially cylindrical passage 25 extends through section 24 and communicates with small opening 22 so that fluid may pass through bore 20 and into passage 25. Passage 25 is sized so that the needle 16 may be press fit therein and thus affixed to hub assembly 10. While the external configuration of hub 15 may take a variety of forms, it is preferable to include a flange 26 around the proximal end to assist in the assembly of the internal components, and to assist in handling both before and after the final unit is completed.

Filter membrane 18 is disposed within tapered bore 20 intermediate large opening 21 and small opening 22. In order to allow sufficient space for a mating hypodermic syringe carrying fluid medicament to subsequently enter tapered bore 20, it is preferable to position filter membrane 18 closer to small opening 22. A first portion 28 of filter membrane 18 extends transversly across bore 20 substantially perpendicular to the longitudinal axis thereof. First portion 28 is substantially circular in shape, so that its periphery essentially conforms to the circular cross-section of bore 20 at the position at which it is located. Thus, it can be seen that all fluids passing through bore 20 into passage 25 also pass through first portion 28 of filter membrane 18. This, of course, provides a final measure of precaution and filtration of fluids entering into a patient.

Extending from first portion 28 is a second portion 30 of filter membrane 18. Second portion 30 is an upturned annular flange integral with the periphery of first portion 28, which faces towards large opening 21 of the bore. Flange 30 has an outside surface 31 which is in substantially circular contact with hub 15 around the internal surface of bore 20. In the preferred embodiment of this invention, filter membrane 18 includes a thin plastic coating laminated on each surface thereof. This laminate, especially on the outside surface 31 of the flange, provides a locking interface between filter membrane 18 and hub 15 in order to provide a secure fit of the filter membrane in the bore. This type filter membrane is flexible and strong, but is not resilient, i.e., it does not exhibit spring tendencies to assume its original shape after being flexed. This flexibility keeps the filter from fracturing during the fabrication of the hub assembly.

Retaining ring 19 is employed to insert filter membrane 18 in bore 20, and also to remain in bore 20 along with the filter membrane to keep the latter securely in place in the completed hub assembly unit. This retaining ring is basically a washer element with a central opening 34 therethrough to allow fluid to pass from bore 20 towards and through filter membrane 18. Ring 19 is substantially circular in cross-section, and has a diameter smaller than large opening 21, but larger than small opening 22. Depending upon where ring 19 will be positioned intermediate the ends of bore 20, its diameter will be selected accordingly. It can be seen that ring 19 has a flat end surface substantially in contact with first portion 28 of the filter membrane, thereby extending transversly across bore 20 in alignment with first portion 28. The periphery of ring 19 is in annular contact with inside surface 32 of flange 30. Ring 19 has been inserted in bore 20 along with filter membrane 18 to a position intermediate the ends thereof whereat the ring diameter and the bore diameter are substantially equal. At this position, ring 19 exerts a radially outward force against flange 30 thereby pressing the flange tightly against hub 15 around bore 20. This force fit allows the filter membrane to remain in place in hub assembly 10 as a completed unit; additionally, and just as importantly, the force fit of the filter membrane therein blocks off the undesirable flow of fluid around the periphery of the filter membrane, thereby channeling all fluids through the filter membrane itself to assure the final filtration of the fluid.

It will also be seen in FIG. 2 that bore 20 includes a step or shoulder 27 formed near the distal end thereof. This shoulder helps orient and seat ring 19 as it secures the filter membrane inside the bore. When the hub includes shoulder 27 therein, the diameter of ring 19 must be coordinated with the bore diameter at the shoulder so that the ring will fit tightly against the internal surface of the hub before being completely seated on the shoulder.

Although many different materials may be selected for fabricating hub 15, the preferable material is plastic, such as polypropylene and the like. Filter membrane 18 is also selected from many different filter media commonly used in conjunction with hypodermic needles. One filter medium which is desirably employed in the present invention is a product known as ACROPOR, an acrylonitrile-polyvinlychloride copolymer reinforced with nylon mesh, manufactured by the Gelman Instrument Co., Ann Arbor, Michigan. The nylon mesh substrate in the ACROPOR filter has a thickness of approximately 0.002 inches (0.005 cm.). The copolymer is laminated on each surface of the nylon mesh, the thickness of each being approximately 0.0015 inches (0.0038 cm.). This filter membrane generally has a pore size of between 0.22 and 5 microns. Ring 19 may also be fabricated from a large selection of materials, but in the embodiment being described is made from rigid nylon. The ring is preferably relatively thin, in the order of 0.03 inches (0.076 cm.), so that it does not take up too much of the tapered bore in a sleeving effect. The small size of the ring not only keeps cost down but also keeps the weight of the hub assembly down while presenting a neat appearance to the eye of the user.

Referring to FIGS. 3-5, there is schematically illustrated the sequential steps of one method of fabricating a filter membrane and inserting it into a hub similar to that described above. Turning first to FIG. 3, a filter medium 40, such as a sheet, film or other supply thereof, is supported on support member 41 or other table or similar member. Support 41 includes a substantially circular hole 42 therethrough, with the hole on one surface of support member 41 having a counterbore 44. The depth of counterbore 44 is generally greater than the thickness of the sheet of filter medium 40 which lies across the surface of support member 41. Positioned above filter medium 40 and aligned with hole 42 and counterbore 44 is a punching member 45. The punching member has a hole 46 therethrough in alignment with hole 42 in support member 41. The outside diameter of punching member 45 is somewhat smaller than the diameter of counterbore 44. In FIG. 4, punching member 45 has moved downwards, for example, in a punch press or similar device (not shown), and in so moving punches out a section 48 of filter medium 41 into counterbore 44 substantially in conformity with the diameter of the counterbore. This section 48 is a substantially flat, circular filter membrane which is to be included in a hub assembly. The diameter of filter section 48 generally depends upon the size of the bore of the hub into which it is to be inserted. However, it has been found preferable to fabricate section 48 with a diameter larger than the large opening of the bore in order to assure proper flange formation and wiping action of the filter as it is inserted therein. At this time and in conjunction with FIG. 4, retaining ring 19 is generally placed into hole 46 so that retaining ring 19 rests over filter membrane section 48.

Turning now to FIG. 5, another support member 49 holds hub 15 therein, for example, by having flange 26 of hub 15 rest on a flat surface of support 49. Support member 41 and the components associated therewith in the previous steps, and support member 49 with hub 15 are brought together so that filter membrane section 48 is aligned with and placed over large opening 21 of hub 15. At this point, filter membrane section 48 is positioned so that its flat surfaces are substantially perpendicular to the longitudinal axis of bore 20. Thus, the elements which will form the hub assembly are now properly positioned for assembly. While FIG. 5 depicts the supported hub being mated with support 41 after filter section 48 has been formed, oftentimes the supported hub is brought into alignment before filter section 48 is punched out, depending upon the structure of the fixture on which the fabrication and insertion is performed.

Ring 19 is now advanced downwardly by rod member 50 which has been inserted into hole 46 of punching member 45 to act as a guide therefor. This downward advance moves ring 19 completely through support member 41, with filter membrane 48 in advance of the downward movement. As the diameter of membrane 48 is larger than hole 42, in order to pass therethrough its periphery is formed into an annular flange 51 facing the opposite direction from which the ring is advancing. The remaining portion 52 of filter membrane 48 extends transversly across bore 20 in surface to surface contact with ring 19. It can be seen that, as ring 19 has a diameter larger than small opening 22 of bore 20 but smaller than large opening 21 of the bore, its advance under pressure from rod member 50 will continue until the position in the bore at which the ring diameter and the bore diameter are substantially equal. If the hub 15 has a step or shoulder in the bore, the ring diameter and its final position in the bore will have been predetermined and coordinated. While advancing into bore 20, as the position of equal diameters is approached, ring 19 exerts a pressing force radially outwardly against flange 51, so that the transverse portion 52 is rendered taut by the wiping action of flange 51 along hub 15 around bore 20. The advance of ring 19 and filter membrane 48 is stopped when the combination of tapered bore 20 and the force pressing against flange 51 provide a secure fit of the filter membrane in the bore.

Thus, the present invention provides a hub assembly in a completed unit, with the filter firmly secured therein in a way to provide filtration of the fluid through the filter itself rather than by paths around its periphery. Furthermore, the present invention provides a method of fabricating the filter membrane and inserting it into the hub.

What is claimed is:

1. A hub assembly for use in the filtration of fluids therethrough comprising: a hub having a bore extending therethrough, said bore being substantially circular in cross-section and tapered in generally frusto-concial fashion thereby defining a large opening at the proximal end thereof and a small opening at the distal end thereof, said small opening adapted to receive means for conducting fluid from said bore; a substantially flat filter membrane in said bore, said filter membrane having a first, substantially circular portion extending transversely across said bore intermediate said ends and having a second, annular portion around the periphery of said first portion, said second portion having an outside surface and an inside surface, said outside surface being in substantially circular contact with the internal surface of said hub; and a retaining ring having an opening therethrough, said ring having a substantially circular cross-section smaller than said large opening but larger than said small opening, said ring extending transversely across said bore and in annular contact with said inside surface of said second portion of said filter, said ring being effective to secure said filter membrane within said bore by pressing said second portion of said filter tightly against said hub.

2. A hub assembly as defined in claim 1 wherein said second portion of said filter is an upturned annular flange extending from said first portion, with said flange facing towards said large opening of said bore.

3. A hub assembly as defined in claim 1 wherein said filter membrane is made of nylon mesh with a copolymer of acrylonitrile and polyvinylchloride on at least one surface thereof.

4. A hub assembly as defined in claim 3 wherein the pore size of said filter membrane is between 0.22 and 5 microns.

5. A hub assembly for use in the filtration of fluids therethrough comprising: a hub having a bore extending therethrough, said bore being substantially circular in cross-section and tapered in generally frusto-conical fashion thereby defining a large opening at the proximal end thereof and a small opening at the distal end thereof, said hub including a section extending from said distal end, said section having a substantially cylindrical passage therethrough communicating with said small opening, said passage adapted to receive a hollow needle for conducting fluid from said bore therethrough; a substantially flat flexible filter membrane in said bore, said filter membrane having a first, substantially circular portion extending transversely across said bore, said filter membrane having a second, annular portion being an upturned annular flange extending from said first portion and facing towards said large opening, said flange having an outside surface and an inside surface, said outside surface being in substantially circular contact with said hub around said bore; and a retaining ring having an opening therethrough, said ring having a substantially circular cross-section smaller than said large opening but larger than said small opening and extending transversely across said bore with a flat surface of said ring in contact with said first portion of said filter, said ring being in annular contact with said inside surface of said flange, said ring being inserted in said tapered bore to secure said filter membrane therein by pressing said flange tightly against said hub around said bore at the position whereat said ring diameter and said bore diameter are substantially equal.

6. A method of fabricating a filter membrane and inserting the same into a hub having a bore extending therethrough, said bore being substantially circular in cross-section and tapered to define a large opening at the proximal end thereof and a small opening at the distal end thereof, comprising: forming a substantially flat, circular filter membrane; inserting said filter membrane into the large opening of said tapered bore so that a first portion thereof is substantially perpendicular to the longitudinal axis of said bore, and a second portion of said membrane is formed, said second portion being an annular flange extending from said first portion along said hub around said bore and facing said large opening; advancing said filter membrane a sufficient distance in said bore and applying a force radially outwardly to press against said flange so that said first portion is rendered taut by the wiping action of said flange along said hub around said bore; and stopping the advance of said filter membrane when the combination of said tapered bore and the force pressing against said flange provide a secure fit of said filter membrane in said bore.

7. A method as defined in claim 6 wherein said filter membrane is formed by punching out a section of filter membrane from a blank of filter medium by a substantially circular punching member.

8. A method as defined in claim 7 wherein said inserting step includes placing a retaining ring over said filter membrane which has been placed over said large opening, said retaining ring having a circular cross-section smaller than said large opening of said bore, but larger than said small opening of said bore, and advancing said retaining ring and said membrane into said bore so that said first, flat portion and said second flange portion are formed, said flange portion lying between the annular surface of said ring and said hub around said bore.

9. A method as defined in claim 8 wherein said ring produces said pressing force against said flange as said ring and filter membrane advance into said bore to the position intermediate the ends thereof where said ring diameter and said bore diameter are substantially equal.

10. A method of fabricating a filter membrane and inserting the same into a hub having a bore extending therethrough, said bore being substantially circular in cross-section and tapered to define a large opening at the proximal end thereof and a small opening at the distal end thereof, comprising:

forming a substantially flat, circular filter membrane by punching out a section from a blank of filter medium, said filter membrane having a diameter larger than said large opening of said bore;

placing said filter membrane over said large opening of said bore so that said flat surfaces are substantially perpendicular to said longitudinal axis of said bore;

placing a retaining ring over said filter membrane, said retaining ring having a circular cross-section smaller than said large opening, but larger than said small opening of said bore; and advancing said ring and said filter membrane into said bore so that a first portion of said filter membrane is formed in surface to surface contact with said ring and extending transversely across said bore, and a second portion of said membrane is formed, said second portion being an annular flange extending from said first, flat portion along said hub around said bore and facing said large opening, said flange portion lying between the annular surface of said ring and said hub; and advancing said filter membrane and said ring a sufficient distance into said bore to the position intermediate the ends thereof whereat the diameter of said ring and the diameter of said bore are substantially equal, whereby said ring exerts a radially outward force against said flange thereby providing a secure fit of said filter membrane in said bore.

11. In a needle assembly for intravenous insertion into a patient's vein of the type having a hollow needle connected to an open-ended hub, wherein the improvement comprises: a hub having a tapered bore extending therethrough, one end of said bore communicating with said needle, the other end being an open end in said hub; a substantially flat filter membrane in said bore having a first portion extending across said bore, and having a second portion extending from said first portion and being in substantial contact with the wall of said hub around said bore; and means within said bore for pressing said second portion into tight contact with said hub around said bore to secure said filter membrane therein.

12. An improved needle assembly as defined in claim 11 wherein said second portion of said filter membrane is an upturned annular flange extending from said first portion, with said flange facing toward said open end of said hub.

* * * * *

UNITED STATES PATENT AND TRADEMARK OFFICE
CERTIFICATE OF CORRECTION

PATENT NO. : 4,127,131

DATED : November 28, 1978

INVENTOR(S) : Vincent Louis Vaillancourt

It is certified that error appears in the above—identified patent and that said Letters Patent is hereby corrected as shown below:

Insert the claim as part of Letters Patent:

-- 13. A method as defined in claim 11 which includes the steps of positioning said filter membrane on a support having a substantially cylindrical hole slightly larger than the circular cross-section of the retaining ring and smaller than the diameter of said filter membrane; locating said membrane above said support and said support above the large opening of said bore so that said membrane and said cylindrical hole are substantially axially centered over said large opening; placing said ring over said membrane while said membrane is positioned on said support; and advancing said ring with said membrane through the cylindrical hole in said support to begin

UNITED STATES PATENT AND TRADEMARK OFFICE
CERTIFICATE OF CORRECTION

PATENT NO. : 4,127,131

DATED : November 28, 1978

INVENTOR(S) : Vincent Louis Vaillancourt

It is certified that error appears in the above—identified patent and that said Letters Patent is hereby corrected as shown below:

forming said annular flange of said membrane. --.

On the Title Page "12 Claims, 5 Drawing Figures" should read -- 13 Claims, 5 Drawing Figures --.

Signed and Sealed this

Twenty-second Day of July 1980

[SEAL]

Attest:

SIDNEY A. DIAMOND

Attesting Officer

Commissioner of Patents and Trademarks